United States Patent
Rana et al.

(10) Patent No.: US 11,311,590 B2
(45) Date of Patent: Apr. 26, 2022

(54) ANTI-INFLAMMATORY BOTANICAL EXTRACT

(71) Applicant: Innophos, Inc., Cranbury, NJ (US)

(72) Inventors: Jatinder Rana, Grand Rapids, MI (US); Kylie Mitchell, Pennington, NJ (US)

(73) Assignee: Innophos, LLC, Cranbury, NJ (US)

( * ) Notice: Subject to any disclaimer, the term of this patent is extended or adjusted under 35 U.S.C. 154(b) by 0 days.

(21) Appl. No.: 17/159,356

(22) Filed: Jan. 27, 2021

(65) Prior Publication Data

US 2021/0145913 A1    May 20, 2021

Related U.S. Application Data

(62) Division of application No. 16/515,104, filed on Jul. 18, 2019, now Pat. No. 10,933,108.

(60) Provisional application No. 62/725,461, filed on Aug. 31, 2018.

(51) Int. Cl.
*A61K 36/22* (2006.01)
*A61K 9/00* (2006.01)
*A61K 31/353* (2006.01)

(52) U.S. Cl.
CPC ............ *A61K 36/22* (2013.01); *A61K 9/0014* (2013.01); *A61K 31/353* (2013.01)

(58) Field of Classification Search
None
See application file for complete search history.

(56) References Cited

U.S. PATENT DOCUMENTS 10,933,108 B2 *    3/2021    Rana ........................ A61P 29/02

OTHER PUBLICATIONS

Chandrasekara (Journal of Agricultural and Food Chemistry (2011), vol. 59, pp. 5006-5014).*

* cited by examiner

*Primary Examiner* — Susan Hoffman
(74) *Attorney, Agent, or Firm* — David LeCroy

(57) ABSTRACT

A botanical extract that exhibits anti-inflammatory activity, wherein the botanical extract is at least an extract from the genus *Anacardium*.

8 Claims, 8 Drawing Sheets

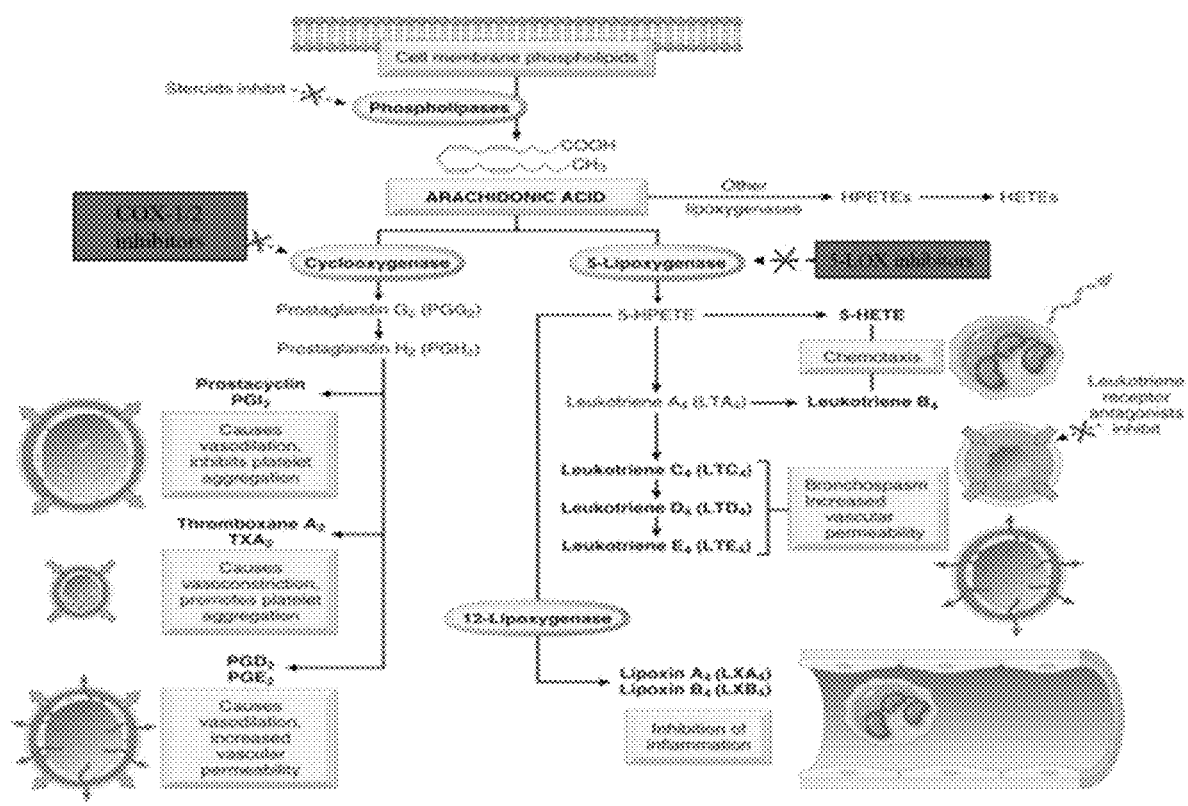
Figure 1 – Arachidonic acid metabolism pathway

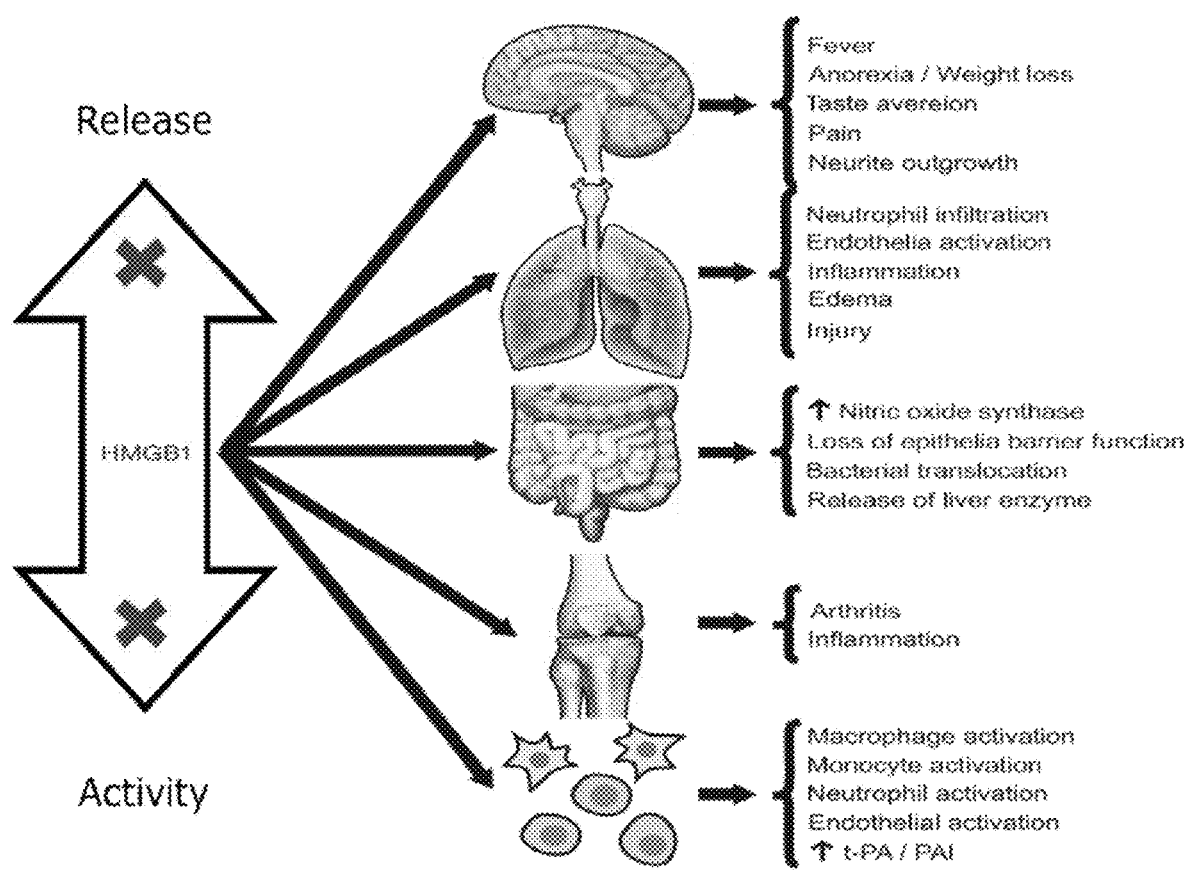
Figure 2 – Illustration of HMGB1-mediated pro-inflammatory responses at various sites

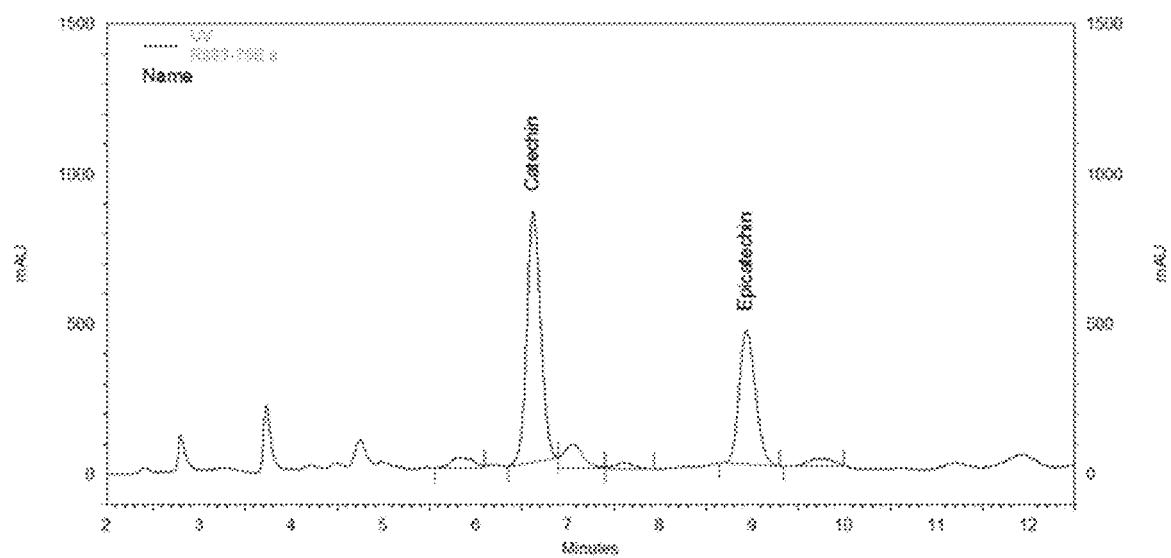
Figure 3 – HPLC Chromatogram of Cashew Testa Extract at 275 nm wavelength

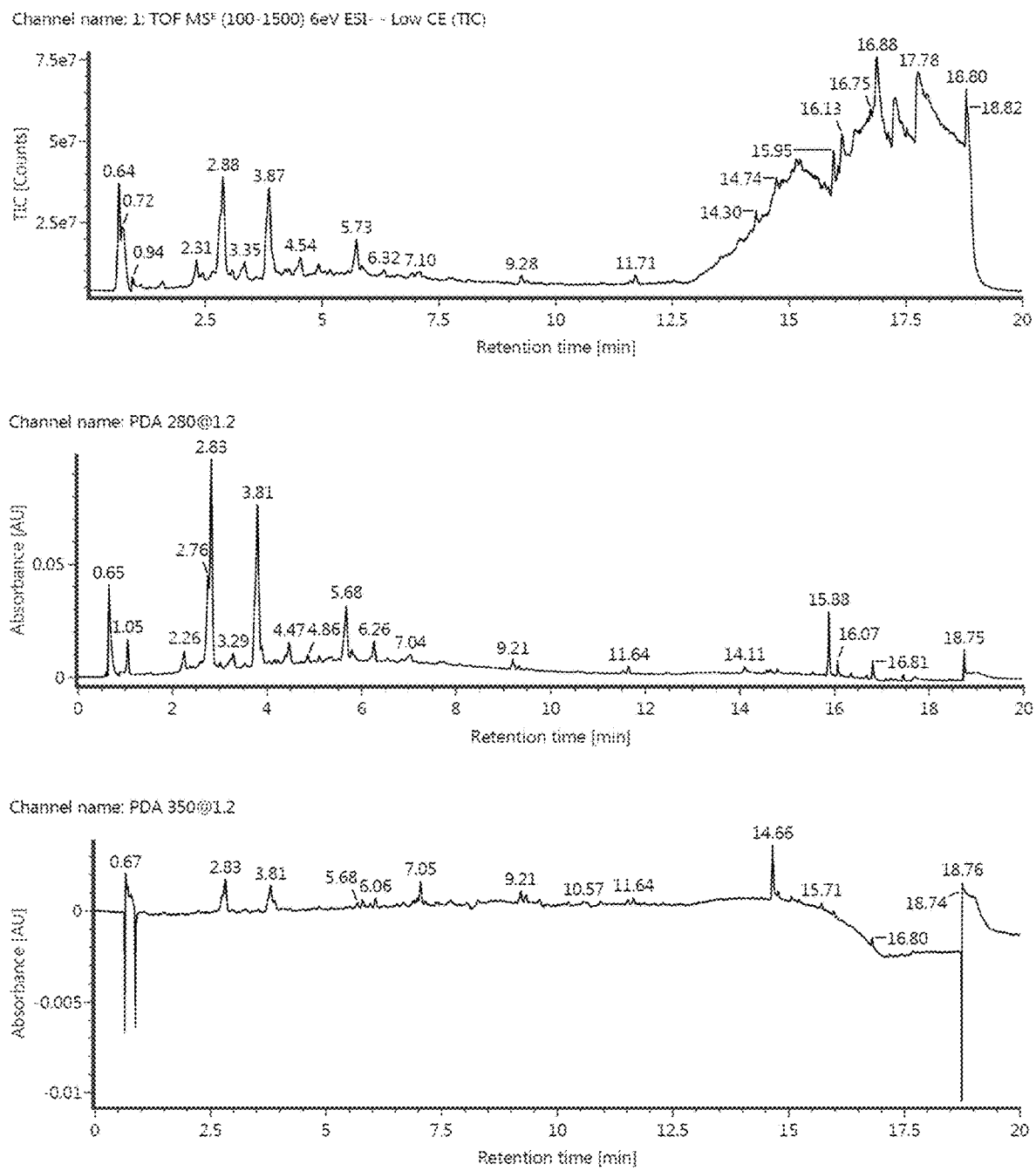
Figure 4 – LC/MS and LC/PDA (280/350 nm) Chromatograms of Cashew Testa Extract

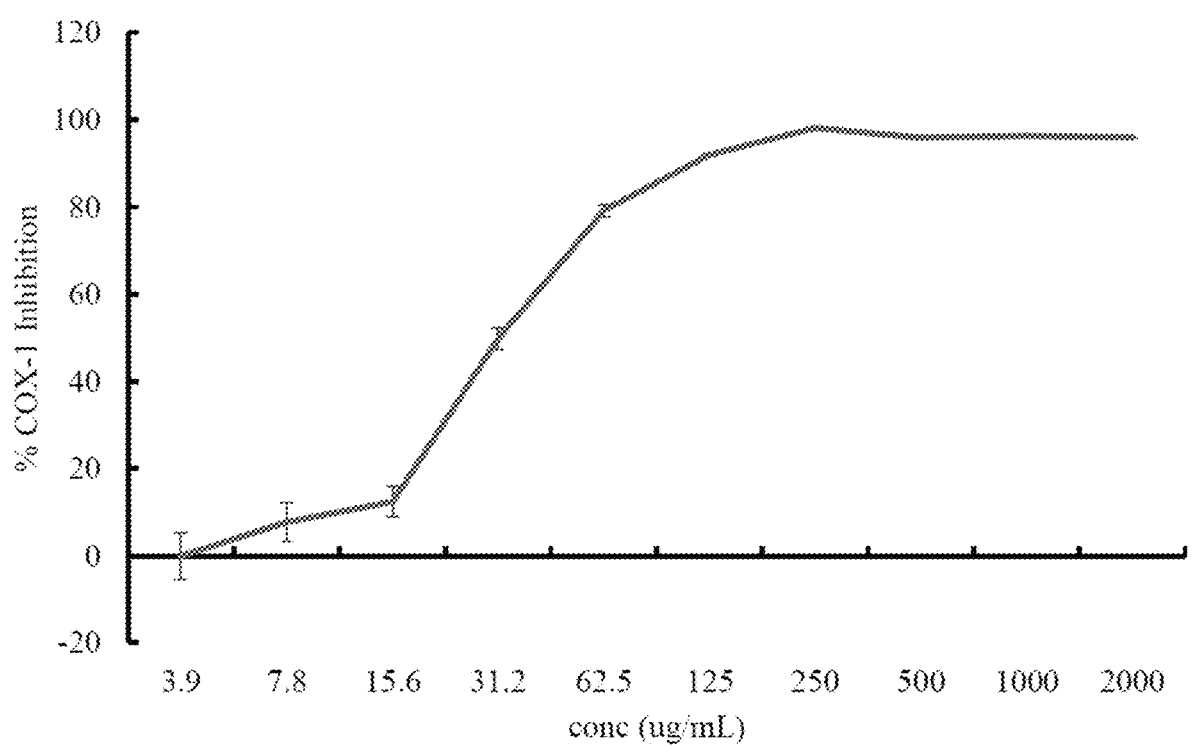
Figure 5 – Cashew Testa Extract COX-1 Inhibition at 10 Concentrations (µg/mL)

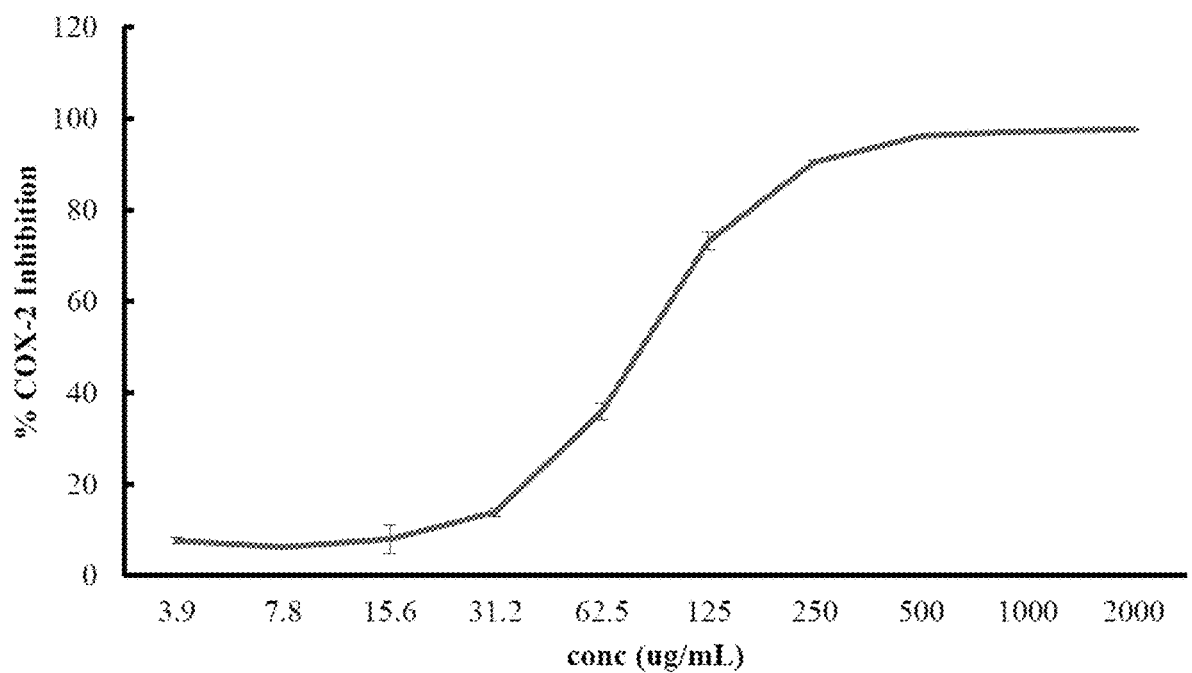
Figure 6 – Cashew Testa Extract COX-2 Inhibition at 10 Concentrations (μg/mL)

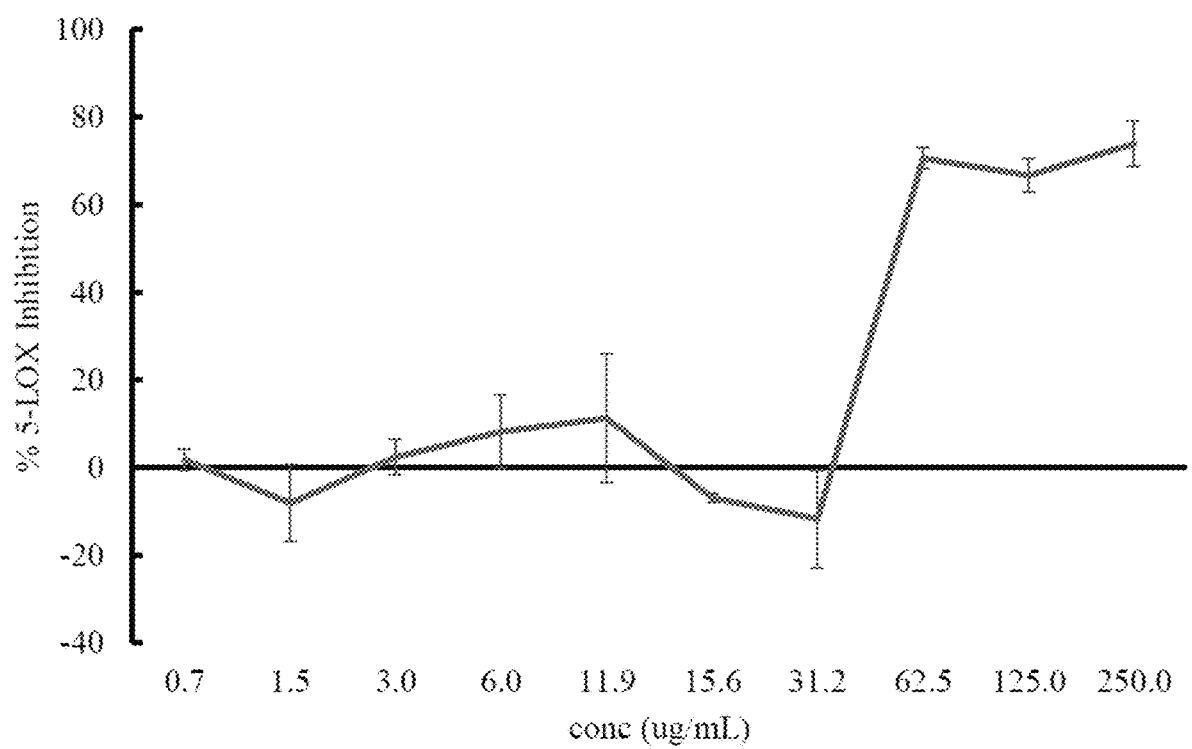
Figure 7 – Cashew Testa Extract 5-LOX Inhibition at 10 Concentrations (µg/mL)

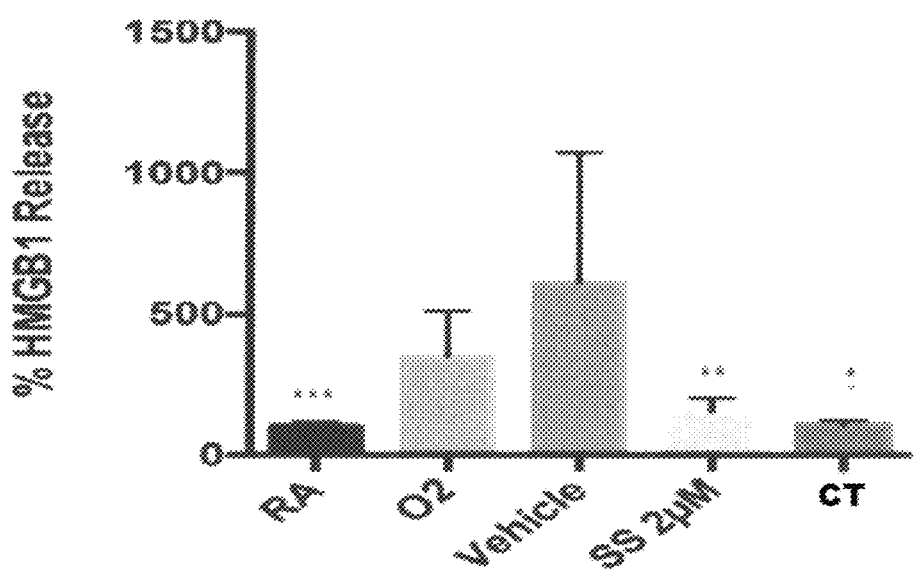
Figure 8 – Detection of HMGB1 accumulation in macrophage cell culture supernatant
(* $p<0.05$,  $p<0.01$, * $p<0.0001$)

ANTI-INFLAMMATORY BOTANICAL EXTRACT

CROSS REFERENCE TO RELATED APPLICATIONS

The present application is a divisional application of U.S. patent application Ser. No. 16/515,104, filed 18 Jul. 2019, now U.S. Pat. No. 10,933,108, which claims the benefit of U.S. Patent Application No. 62/725,461, filed 31 Aug. 2018, the disclosure of which is incorporated herein in its entirety by reference.

BACKGROUND OF THE INVENTION

Field of the Invention. The present invention generally relates to a botanical extract that exhibits anti-inflammatory activity, and compositions comprising such an extract.

Arachidonic acid and its metabolites are important mediators of inflammation. Arachidonic acid ('AA') is a component of membrane phospholipids where the rate-limiting step in the formation of its metabolites depends on its release from the cell membrane phospholipid pool mediated through activation of phospholipases. Thereafter, it can be metabolized by one of two pathways—by cyclooxygenase ('COX') to yield eicosanoids such as prostaglandins ('PGE2'), prostacyclins, and thromboxanes, or it can be metabolized by 5-lipoxygenase ('5-LOX') to result in the production of leukotrienes and lipoxins. These eicosanoids serve as intracellular messengers and play significant roles in the regulation of signal transduction in pain and inflammatory responses. An illustration of the arachidonic acid metabolism pathway is provided in FIG. 1.

Cyclooxygenase—a prostanoid synthase also known as prostaglandin-endoperoxide synthase (PTGS, EC 1.14.99.1)—is an enzyme that is responsible for the formation of important biological mediators called prostanoids, including prostaglandins, prostacyclin and thromboxane. COX is the central enzyme in the biosynthetic pathway to prostanoids from arachidonic acid. There are two known isoenzymes—COX-1 and COX-2. COX-1 represents the constitutive isoform responsible for production of prostaglandins involved in physiological functions such as protection of the gastric mucosa and maintenance of renal perfusion. COX-2 is not expressed under normal conditions in most cells, but elevated levels are found during inflammation. COX-2 is the dominant isozyme in inflamed tissues, where its induction can be facilitated by several pro-inflammatory cytokines, including interleukin-1 ('IL-1') and tumor necrosis factor ('TNF-α'). Pharmacological inhibition of COX by non-steroidal anti-inflammatory drugs (NSAID) can provide relief from the symptoms of inflammation and pain.

Therefore, to prevent the unwanted side effects, it seems practical to inhibit COX-2 selectively for its analgesic and anti-inflammatory effects without affecting important physiological processes controlled by the prostaglandins formed by COX-1. Still, there are reports that associate the synergistic effect of COX-2 as a constitutive isoenzyme in maintaining renal blood flow and the glomerular filtration rate suggesting its selective inhibition may lead to some adverse effects. These effects were experienced by subjects in clinical trials wherein selective COX-2 inhibitors (e.g., celecoxib and rofecoxib) provided similar efficacy to that of traditional NSAIDs in osteoarthritis and rheumatoid arthritis pain with better gastric tolerability and equivalent to NSAIDs in renal side effects. Therefore, it is reasonable to assume and have a compound strong enough to cause inhibition of these isoenzymes yet moderate enough to avoid the unnecessary adverse consequences, as opposed to a complete selective inhibition of either of the enzymes.

Increased expression of COX-2, and hence synthesis of its product PGE2, has also been found to be strongly associated with the induction of MMP-9, which is a key player in cancer, cardiovascular disease, and inflammation. Therefore, inhibition of COX-2 enzyme may result in regulation of MMP-9 expression and activity that may modulate invasion and migration of cancer cells, prevent or delay the progression of atherosclerosis and stabilize plaques, regulate macrophage proteinase expression, prevent chronic periodontitis and gingivitis, and control remodeling of liver disease, among others.

The other segment of the Arachidonic acid ('AA') metabolism pathway is through the 5-lipoxygenase ('5-LOX') pathway, where leukotrienes (LTB4, LTC4, LTD4, and LTE4) derived from LTA4 are the end bioactive metabolites. LTC4 and its products LTD4 and LTE4 act on smooth muscle cells of bronchi and blood vessels, where their biologic effects suggest their role in allergic reaction and inflammatory processes. For example, in asthma they cause bronchoconstriction, vasoconstriction, and increased vascular permeability; thus, they are previously known as slow-reacting substances of anaphylaxis. The other component of this pathway—LTB4—is a potent chemotactic factor of neutrophils. While the specific inhibitor of the 5-LOX enzyme—Zileuton—provides effective intervention of asthma attacks where the anti-inflammatory and antibronchospastic effects work together, single therapeutic modality for 5-LOX modulators seem insufficient.

Preferably, anti-inflammatory products encompass inhibition of both main metabolic pathways of Arachidonic acid ('AA') metabolism, possessing a wide range of anti-inflammatory activities while also having a better safety profile.

Another mediator of inflammation which acts as cytokine and is secreted by immune cells are High Mobility Group Box 1 proteins ('HMGB1'), also known as high-mobility group protein 1 ('HMG-1') and amphoterin. HMGB1 is a protein that in humans is encoded by the HMGB1 gene. Like the histones, HMGB1 is among the most important chromatin proteins. HMGB1 is a 30 kDa nuclear and cytosolic protein, and is a self-derived immune activator that has multiple functions in the regulation of immunity and inflammation.

HMGB1 can be released actively by innate immune cells such as macrophages, monocytes, and dendritic cells at the time of inflammation and injury. For example, macrophages and monocytes actively release HMGB1 in a time- and dose-dependent manner in response to stimulation with exogenous bacterial endotoxin (e.g., lipopolysaccharide, or LPS), or endogenous pro-inflammatory cytokines such as tumor necrosis factor ('TNF-α'), Interleukin-1 beta ('IL-1β'), and Interferon gamma ('IFN-γ').

HMGB1 can also be released passively by necrotic or damaged cells, and is capable of inducing an inflammatory response by communicating the insult to the neighboring immune cells, allowing the innate immune cells to both respond to injury and to further induce inflammation. HMGB1 proteins trigger intracellular signaling through receptor for advanced glycosylation end products ('RAGE') and/or Toll-like receptors (TLR-2/4), which in turn activate various signaling pathways as mitogen-activated protein kinase ('MARK') pathways and subsequent nuclear factor kappa-light-chain-enhancer of activated B cells ('NF-κB')

mediating inflammation, leading to the expression of various leukocyte adhesion molecules, pro-inflammatory cytokines, and chemokines.

HMGB1 plays significant roles in inflammatory activity and is involved in a wide range of immune responses. HMGB1 induces maturation and migration of dendritic cells ('DCs'), as well as the activation of these cells and monocytes to produce pro-inflammatory cytokines such as TNF-α, IL-1β, IL-6, and macrophage inflammatory protein 1 ('MIP-1'). HMGB1 also serves as a chemotactic factor for monocytes, macrophages, neutrophils, and DCs to sustain inflammation and elicit innate immune response.

HMGB1 is considered a lead example of a danger signal that originates from the damaged self instead of from invading pathogens. HMGB1 mediates activation of innate receptors resulting in the amplification of inflammatory responses through the release of cytokines, which in turn induce the release of additional HMGB1, further promoting the induction of these mediators. While pro-inflammatory cytokines such as TNF-α, IL-1β, and IFN-γ are known to mediate the early phases of inflammation, HMGB1 is considered as the late phase dictator in sepsis and tissue injury.

Targeting HMGB1 may be a pragmatic approach for therapeutic interventions in inflammatory diseases as it has been identified as a crucial mediator in the pathogenesis of many diseases, including sepsis, arthritis, cancer, and diabetes. For example, the level of HMGB1 has been found to be elevated in (1) synovial fluid of patients with rheumatoid arthritis, (2) septic patients who did not survive compared to those who did survive, (3) invasion and metastasis of solid tumors, and (4) diabetes and its complications.

As a consequence, many pharmacologic agents have been studied for their potential to inhibit release of HMGB1 or HMGB1 activity (see, FIG. 2). These include traditional herbal medicines such as aqueous extracts of dong guai or dang gui ("female ginseng"—*Angelica sinensis*), Green tea (*Camellia sisensis*), and Danshen ("red sage" or "Chinese sage"—*Saliva miltorrhiza*), which have been found to inhibit endotoxin-induced HMGB1 release, as well as protect animals against experimental sepsis.

Accordingly, phytomedicine plays an important role in the management of most of these diseases, with plants being a potential source of natural antioxidants. Studies have shown that the consumption of polyphenolic compounds found in tea, herbs, fruits, and vegetables is associated with low risk of these diseases. Consequently, there is a growing research interest in plants that exhibit anti-inflammatory activity and health-promoting phytoconstituents as potential therapeutic agents. Medicinal plants can provide a safe, cost-effective, ecological alternative to chemical antioxidants, which can be toxic on prolonged exposure.

The cashew tree (*Anacardium occidentale Linn*) is originally from the Amazon, and has subsequently been transplanted to India, Eastern Africa, and other countries for cultivation. The tree produces a very peculiar apple or fruit in the form of a swollen peduncle. Externally at the end of this peduncle the cashew nut grows in its own grey colored kidney-shaped hard shell. This shell has a soft leathery outer skin and a thin hard inner skin referred to as the husk or testa, which surrounds the kernel. Between these two skins is a honeycomb structure containing the cashew nut shell liquid. This liquid comprises anacardic acid, cardanol, and cardol, among other ingredients. Anacardic acid is a salicylic acid, while cardanol and cardol are substituted phenols.

The various parts of the fruit have been studied for their uses. In addition to being an edible food, the juice from the cashew apple is used in beverages, while the fruit extract has shown benefit in weight management. Cashew nut shell liquid has been extracted for various industrial and agricultural applications, include friction linings, paints, laminating resins, rubber compounding resins, cashew cements, polyurethane based polymers, surfactants, epoxy resins, foundry chemicals, chemical intermediates, insecticides, and fungicides. Cashew testa has been used in tanning materials.

As noted above, there is a need for effective, nontoxic, natural compounds with anti-inflammatory activity. The present invention provides one such solution.

BRIEF SUMMARY OF THE INVENTION

Provided herein is a botanical extract composition comprising catechins, wherein the extract has been standardized to a catechin content of about 15.0 wt % or greater, based on total weight of the extract. The botanical extract composition exhibits anti-inflammatory activity and comprises at least an extract from the genus *Anacardium*. Preferably the botanical extract is at least an extract from *Anacardium occidentale L*. More preferably, the botanical extract is from at least the testa of the fruit of *Anacardium occidentale L*.

In one embodiment, the present invention is directed towards an extract of the testa of the fruit of *Anacardium occidentale L*. comprising about 15.0 wt % or greater catechins, based on total weight of the extract.

In a further embodiment, the present invention provides a composition comprising the botanical extract of the testa of *Anacardium occidentale L*, wherein the botanical extract exhibits anti-inflammatory activity. The botanical extract can be present in the composition in an amount of about 4 μg/mL or greater. Preferably, the botanical extract is present in the composition in an amount of about 4 μg/mL to about 2000 μg/mL. More preferably, the botanical extract is present in the composition in an amount of about 15 μg/mL to about 250 μg/mL.

Regarding the anti-inflammatory activity of the botanical extract of the composition, in one aspect compositions containing the botanical extract of the testa of *Anacardium occidentale L*. inhibit COX-1 activity. Preferably for such compositions inhibiting COX-1 activity, the botanical extract is present in the composition in an amount of about 15 μg/mL to about 250 μg/mL.

In another aspect, compositions containing the botanical extract of the testa of *Anacardium occidentale L*. inhibit COX-2 activity. Preferably for such compositions inhibiting COX-2 activity, the botanical extract is present in the composition in an amount of about 30 μg/mL to about 250 μg/mL.

In even another aspect, compositions containing the botanical extract of the testa of *Anacardium occidentale L*. inhibit 5-LOX activity. Preferably for such compositions inhibiting 5-LOX activity, the botanical extract is present in the composition in an amount of about 32 μg/mL to about 250 μg/mL.

In a further aspect, compositions containing the botanical extract of the testa of *Anacardium occidentale L*. inhibit HMGB1 activity. In one embodiment for such compositions inhibiting HMGB1 activity, the botanical extract is present in the composition in an amount of about 50 μg/mL.

In another aspect, compositions containing the botanical extract of the testa of *Anacardium occidentale L*. inhibit COX-1 activity, COX-2 activity, 5-LOX activity, and HMGB1 activity.

Compositions containing the botanical extract of the testa of *Anacardium occidentale L*. can further comprise a pharmaceutically acceptable carrier. Non-limiting examples of such compositions include dietary supplements and topical compositions.

BRIEF DESCRIPTION OF THE SEVERAL VIEWS OF THE DRAWINGS

FIG. 1 is a general illustration of the Arachiconic acid metabolism pathway.

FIG. 2 is a general illustration of HMGB1-mediated pro-inflammatory responses at various sites.

FIG. 3 is an HPLC chromatogram of cashew testa extract at 275 nm wavelength over a retention time of from 0 minutes (start) to 20 minutes.

FIG. 4 is LC/MS and LC/PDA (wavelengths of 280 and 350 nm) chromatograms of cashew testa extract.

FIG. 5 is a graph illustrating percentage COX-1 inhibition using cashew testa extract at various concentrations.

FIG. 6 is a graph illustrating percentage COX-2 inhibition using cashew testa extract at various concentrations.

FIG. 7 is a graph illustrating percentage 5-LOX inhibition using cashew testa extract at various concentrations.

FIG. 8 is a bar graph illustrating the detection of HMGB1 (% release) in macrophage cell culture supernatant at room atmosphere (21% $O_2$) ('RA'), 95% $O_2$ ('O2') without cashew testa extract, DMSO ('Vehicle'), positive control sodium salicylate ('SS 2 µM'), and 95% $O_2$ with cashew testa extract ('CT').

DETAILED DESCRIPTION OF THE INVENTION

The present invention is based on the surprising discovery that the testa of the cashew (*Anacardium occidentale Linn*) is substantially high in certain flavonoids. In particularly, it has been discovered that the extract of cashew testa comprises catechin and epicatechin as major components, as well as procyanidins. Data noted herein demonstrates that cashew testa extract may have anti-inflammatory applications.

For the present application, the term "composition" refers to a product that treats, improves, promotes, increases, manages, controls, maintains, optimizes, modifies, reduces, inhibits, or prevents a particular condition associated with a natural state, biological process or disease or disorder. For example, a composition improves the inhibition of oxidation and/or reduces inflammation, and the like in a subject. The term composition includes, but is not limited to, pharmaceutical (i.e., drug), over-the counter (OTC), cosmetic, food, food ingredient or dietary supplement compositions that include an effective amount of an extract, at least one component thereof, or a mixture thereof. Exemplary compositions include cream, cosmetic lotion, pack or powder, or as an emulsion, lotion, liniment foam, tablets, plasters, granules, or ointment. Compositions can also include beverages, for example, beverages infused with an effective amount of an extract, or a tea satchel containing an effective amount of an extract. Non-limiting examples of food compositions containing an effective amount of an extract include baked goods, protein powders, meat products, dairy products, and confectionary.

As used herein, the term "extract" or "botanical extract" refers to a solid, viscid, or liquid substance or preparation that includes one or more active ingredients of a substance of at least the plant genus *Anacardium* (e.g., *Anacardium humile, Anacardium othonianum, Anacardium giganteum, Anacardium nanum, Anacardium negrense*, and/or *Anacardium occidentale*), preferably *Anacardium occidentale L*. Preferably, the active ingredient is derived from the extract of the testa of the cashew. The extract is prepared using a solvent such as water, lower alcohols of 1 to 4 carbon atoms (e.g., methanol, ethanol, butanol, etc.), ethylene, acetone, hexane, ether, chloroform, ethylacetate, butylacetate, dichloromethane, N,N-dimethylformamide ('DMF'), dimethylsulfoxide ('DMSO'), 1,3-butylene glycol, propylene glycol, and combinations thereof, but also a fraction of the crude extract in such a solvent. So long as it assures the extraction and preservation of the active ingredient(s), any extraction method may be employed.

As used herein, the term "effective amount" or "therapeutically effective amount" of a pure compound, composition, extract, extract mixture, component of the extract, and/or active agent or ingredient, or a combination thereof refers to an amount effective at dosages and for periods of time sufficient to achieve a desired result. For example, the "effective amount" or "therapeutically effective amount" refers to that amount of a pure compound, composition, extract, botanical extract, extract mixture, botanical extract mixture, component of the extract, and/or active agent or ingredient, or a combination thereof of this invention which, when administered to a subject (e.g., mammal, such as a human), is sufficient to effect treatment, such as improving the inhibition of oxidation and/or reducing inflammation, and the like in a subject. The amount of a composition, extract, botanical extract, extract mixture, botanical extract mixture, component of the extract, and/or active agent or ingredient of this disclosure that constitutes an "effective amount" or "therapeutically effective treatment" will vary depending on the active agent or the compound, the condition being treated and its severity, the manner of administration, the duration of treatment, or the age of the subject to be treated, but can be determined routinely by one of ordinary skill in the art having regard to his own knowledge and to this disclosure.

The term "pharmaceutically acceptable" means those drugs, medicaments, extracts or inert ingredients, which are suitable for use in contact with the tissues of humans and lower animals without undue toxicity, incompatibility, instability, irritation, and the like, commensurate with a reasonable benefit/risk ratio.

The terms "administer", "administered", "administers", and "administering" are defined as providing a composition to a subject via a route known in the art, including but not limited to intravenous, intra-arterial, oral, parenteral, buccal, topical, transdermal, rectal, intramuscular, subcutaneous, intraosseous, transmucosal, or intraperitoneal routes of administration. In preferred embodiments, oral routes of administering a composition are suitable.

As used herein, the term "subject" or "individual" includes mammals to which a composition may be administered. Non-limiting examples of mammals include humans, non-human primates, canines, felines, equines, bovines, rodents (including transgenic and non-transgenic mice) or the like. In some embodiments, the subject is a non-human mammal, and in some embodiments, the subject is human.

As used herein, the term "carrier" refers to a composition that aids in maintaining one or more plant extracts in a soluble and homogeneous state in a form suitable for administration, which is nontoxic and which does not interact with other components in a deleterious manner.

Unless indicated otherwise, all proportions and percentages recited throughout this disclosure are by weight.

The present invention provides a botanical extract that exhibits anti-inflammatory activity. More particularly, the present invention is directed towards a botanical extract of the cashew testa from the genus Anacarium. Such botanical extracts have been found to exhibit anti-inflammatory activity.

As previously stated, useful anti-inflammatory botanical extracts according to the present invention include botanical extracts from the genus *Anacardium*. More particularly, the extract is a botanical extract chosen from one or more of the species *Anacardium humile, Anacardium othonianum, Anacardium giganteum, Anacardium nanum, Anacardium negrense*, and/or *Anacardium occidentale*. Preferably, the botanical extract is from the species *Anacardium occidentale L*. In one embodiment, the botanical extract is from the testa of the species *Anacardium occidentale L*.

Anti-inflammatory compositions according to the present invention may include one or more compounds that may function as active ingredients. The compound may be a component of the botanical extract. For example, the compound can be a phytochemical present in the plant from which the plant extract is obtained. The compound may be at least partially responsible for exhibiting anti-inflammatory activity. The compound can be any compound capable of inhibiting inflammation. In one embodiment, the compound is chosen from the phytochemicals catechins, epicatechins, and/or procyanidins (e.g., A, B, trimer, tetramer).

Generally, one or more parts of a plant can be used to produce a plant extract including, but not limited to, the root, the stem, the leaf, the flower, the fruit, the seed, and the testa of the seed. In the present invention, at least the testa of the seed is used—alone or with other plant parts—to produce the plant extract. The testa from the *Anacardium* plant can be commercially obtained from various sources. The extract of the cashew testa can be obtained using any suitable extraction technique.

In this regard, one or more parts of the plant, particularly the testa of the plant, can be collected and milled. Thereafter, the milled material can be extracted using a suitable solvent. The solvent can be removed in a concentration step. For example, the extracted material can be screened or filtered to create a supernatant and a cake. The cake can be pressed to remove a substantial portion of the liquid, which can be added to the supernatant. The cake can then be dehydrated and used as a fiber source. The supernatant can be distilled to remove the solvent or a portion thereof, to form a plant extract liquid concentrate. The removed solvent can be recycled. The concentrate can be dried (e.g., by spray drying) to provide a dried plant extract. This dried plant extract can be assayed and/or standardized as described herein. Preferably, the dried plant extract is derived from *Anacardium occidentale*, particularly the testa of the plant *Anacardium occidentale L*.

Suitable solvents for the extraction process include water, alcohol, or mixtures thereof. Exemplary alcoholic solvents include, but are not limited to, $C_1$-$C_7$ alcohols (e.g., methanol, ethanol, propanol, isopropanol, and butanol), hydro-alcohols or mixtures of alcohol and water (e.g., hydroethanol), polyhydric alcohols (e.g., propylene glycol and butylene glycol), and fatty alcohols. Any of these alcoholic solvents can be used in the form of a mixture. In one embodiment, the plant extract is extracted using ethanol, water, or a combination thereof (e.g., a mixture of about 70% ethanol and about 30% water). In another embodiment, the plant extract is extracted using only water.

In one embodiment, the plant extract can be obtained using an organic solvent extraction technique. In another embodiment, solvent sequential fractionation can be used to obtain the plant extract. Total hydro-ethanolic extraction techniques can also be used to obtain the plant extract. Generally, this is referred to as a lump-sum extraction.

Total ethanol extraction can also be used. This technique uses ethanol as the solvent. This extraction technique can generate a plant extract having fat soluble and/or lipophilic compounds in addition to water soluble compounds.

Another example of an extraction technique that can be used to obtain the plant extract is supercritical fluid carbon dioxide extraction ('SFE'). In this extraction procedure, the material to be extracted may not be exposed to any organic solvents. Rather, carbon dioxide can be used as the extraction solvent—with or without a modifier—in super-critical conditions (>31.3° C. and >73.8 bar). Those skilled in the art will appreciate that temperature and pressure conditions can be varied to obtain the best yield of extract. This technique can generate an extract of fat soluble and/or lipophilic compounds, similar to a total hexane and ethyl acetate extraction technique.

The plant extract generated in the process can include a broad variety of phytochemicals present in the extracted material. The phytochemicals can be fat soluble or water soluble. Following collection of the extract solution, the solvent can be evaporated, resulting in the extract. The plant extract can be standardized to a specified amount of a particular compound. For example, the plant extract can be standardized to a specified amount of an active ingredient or phytochemical. In one embodiment, the plant extract is standardized to a catechin content of about 15.0 wt % or greater, based on total weight of the extract.

The amount of plant extract present in the inflammation inhibiting composition can depend upon several factors, including the desired level of inflammation inhibition, the inflammation inhibiting level of a particular plant extract or component thereof, and other factors. Preferably, the plant extract is present in an amount of from about 0.005 wt % or greater, for example, from about 0.005 wt % to about 50.00 wt %, based on total weight of the composition.

The anti-inflammatory composition can include one or more acceptable carriers. The carrier can aid in enabling incorporation of the plant extract into an anti-inflammatory composition having a suitable form for administration to a subject. A wide number of acceptable carriers are known in the art, and the carrier can be any suitable carrier. The carrier is preferable suitable for administration to animals, including humans, and can be able to act as a carrier without substantially affecting the desired activity of the plant extract and/or any active ingredient. The carrier can be chosen based upon the desired administration route and dosage form of the composition.

Suitable dosage forms include liquid and solid forms. In one embodiment, the composition is in the form of a gel, a syrup, a slurry, or a suspension. In another embodiment, the composition is in a liquid dosage form such as a drink shot or a liquid concentrate. In a further embodiment, the composition is present in a solid dosage form, such as a tablet, a pill, a capsule, a dragée, or a powder. When in liquid or solid dosage form, the composition can be in a food delivery form suitable for incorporation into food for delivery. Examples of suitable carriers for use in solid forms (particularly tablet and capsule forms) include, but are not limited to, organic and inorganic inert carrier materials such as gelatin, starch, magnesium stearate, talc, gums, silicon dioxide, stearic acid, cellulose, and the like. The carrier can be substantially inert.

As an example, silicified microcrystalline cellulose can be used as a carrier or binder. Silicified microcrystalline cellulose is a physical mixture of microcrystalline cellulose and colloidal silicon dioxide. One such suitable form of silicified microcrystalline cellulose is ProSolv SMCC® 90, available from Penwest Pharmaceutical Co., Patterson, N.J. Silicon dioxide, in addition to that provided by the silicified microcrystalline cellulose, may be added to the composition as a processing aid. For example, silicon dioxide can be included as a glidant to improve the flow of powder during compression in the manufacturing of solid dosage units, such as tablet.

In another embodiment, the carrier is at least a functional carrier such as buckwheat or spelt. By the addition of functional carriers into the composition, additional benefits may be provided such as lower glycemic index compared to standard carriers such as those mentioned above. Further, functional carriers can be allergen free (e.g., buckwheat), and by adding them into the production process, the botanical extracts of the invention may benefit from the flavonoids of these functional carriers, such as rutin and quercetin. Further, the high fiber content of these functional carriers may also facilitate and regulate intestinal transit. Finally, the added mineral benefit of selenium found in spelt may aid in metabolism.

The anti-inflammatory composition can include other inert ingredients, such as lubricants and/or glidants. Lubricants aid in the handling of tablets during manufacturing, such as during ejection from dies. Glidants improve powder flow during tablet compression. Stearic acid is an example of an acceptable lubricant/glidant.

The anti-inflammatory composition can be made in solid dosage form, such as tablets and capsules. This form provides a product that can be easily transported by an individual to a place of eating, such as a restaurant, and taken prior to, during, or after consumption of a foodstuff. The composition can be formulated into dosage units containing suitable amounts of the plant extract and/or active ingredient that permit an individual to determine an appropriate number of units to take based upon appropriate parameters, such as body weight, foodstuff size, or carbohydrate (e.g., sugar) content.

In one embodiment, the botanical extract is present in the composition in a therapeutically effective amount, such as an amount of about 4.0 µg/mL or greater, preferably from about 4.0 µg/mL to about 2000.0 µg/mL, more preferably from about 20.0 µg/mL to about 1000.0 µg/mL, even more preferably from about 25.0 µg/mL to about 750 µg/mL. The composition can be administered, for example, in a dosage of from about 4.0 µg/mL to about 2000.0 µg/mL per day of the plant extract. The composition can be administered as a single dose, or in multiple doses. In one example, the compound is administered in up to three doses per day. For example, the compound may be administered prior to a meal, during a meal, or after a meal. In one embodiment, the composition is a dietary supplement having anti-inflammatory properties containing cashew testa extract in a therapeutically effective amount.

The dosage can be chosen to provide a level of inhibitory effect in a single unit that may be effective for some individuals and/or some foodstuffs, while also allowing for relatively simple dosage increases to provide other levels of inhibitory effects that can be effective for other individuals and/or other foodstuffs.

The inhibiting composition can be in a form adapted for oral ingestion. This form can be configured as a single dosage form intended to provide a specified dose of the plant extract. For example, the single dosage form can be a powder, a pill, a tablet, a capsule, or a drink shot. The single dosage form can include, for example, from about 4.0 µg/mL to about 2000.0 µg/mL of the plant extract.

EXAMPLES

Examples—Materials and Chemical Profiling

Example 1—Preparation of 70% Ethanol Extracts from Cashew Testa

Dried cashew testa powder (*Anacardium occidentale* L.) (60 g) was loaded into three 100 ml stainless steel tubes and extracted twice using a solvent of 70% ethanol in DI water with a Thermo Scientific™ Dionex™ ASE 350 Accelerated Solvent Extractor at a temperature of 80° C. and pressure of 1500 psi. The extract solution was filtered and collected. The combined ethanol extract solution was evaporated with a rotary evaporator under vacuum to give a crude cashew testa extract.

The extraction results are provided in the following Table 1—

TABLE 1

| | Extraction of cashew testa | | |
|---|---|---|---|
| Plant Part | Plant Powder (g) | Extract Weight (g) | Extraction Yield (wt %) |
| Testa | 60 | 23.78 | 39.63% |

Example 2—Catechin Quantification of Cashew Testa Extract

Free catechins present in the cashew testa extract were determined using a C18 reversed-phase column (Luna® 5 µm C18(2) 100 Å LC Column 250×4.6 mm, available from Phenomenex®, Torrance, Calif., U.S.) together with an Hitachi high performance liquid chromatograph with photodiode array detector ('HPLC/PDA'). For mobile phase A, the solvent was 0.10% phosphoric acid ('$H_3PO_4$') in water, and for mobile phase B, the solvent B was acetonitrile ('ACN'), which was used for elution at a flow rated of 1.0 ml/min with UV absorbance at 275 nm and a column temperature of 35° C. Catechin reference standards used were from Sigma-Aldrich Co. The reference standards were dissolved in methanol ('MeOH'): 0.1% $H_3PO_4$ (1:1 ratio) with catechin (C1251) at a concentration of 0.5 mg/ml and epicatechin (E1753) at 0.1 mg/ml. Testing samples were prepared at 2 mg/ml in 50% MeOH in 0.1% $H_3PO_4$ in a volumetric flask and sonicated until dissolved (approximately 10 minutes), and then cooled to room temperature, mixed well, and filtered through a 0.45 µm nylon syringe filter. HPLC analysis was performed by injecting a 20 µl sample into the HPLC. Table 2 below provides the gradient table of HPLC analytical method—

TABLE 2

Gradient Table of HPLC Analytical Method

| Time (min) | Mobile Phase A | Mobile Phase B |
| --- | --- | --- |
| 0.0 | 85.0 | 15.0 |
| 7.0 | 85.0 | 15.0 |
| 12.0 | 10.0 | 90.0 |
| 16.5 | 10.0 | 90.0 |
| 16.6 | 85.0 | 15.0 |
| 24.0 | 85.0 | 15.0 |

HPLC Catechin quantification results in cashew testa extract provided a catechin content of 9.40% and an epicatechin content of 6.12%, for a total catechin content of 15.52% by weight, based on total weight of the extract. Accordingly, the cashew testa extract can be standardized to a total catechin content of about 15.00% or greater by weight, based on total weight of the extract. The HPLC chromatogram for cashew testa extract at 275 nm wavelength is provided in FIG. 3.

Example 3—Chemistry Profiling of Cashew Testa Extract

Flavonoid compounds present in the cashew testa extract were determined using ultra high pressure liquid chromatography ('HPLC') and mass spectrometry (ACQUITY® UPLC I-Class and XEVO® GS-XT-QT of system, both available from Water Corporation, Milford, Mass. U.S.A.). Column used was an ACQUITY® UPLC HSS T3 2.1×100 mm, 1.8 µm, with a column temperature of 40° C. and a sample temperature of 15° C. For the mobile phase, Solvent A was 10% acetonitrile ('ACN') in water (0.1% Formic Acid), and Solvent B was ACN. The acquisition range was 100-1500 Daltons ('Da'), and the acquisition mode was electrospray ionization ('ESI') (−). Table 3 below provides the HPLC conditions—

TABLE 3

HPLC conditions for analyzing cashew testa extract

| Run Time (min) | Injection Volume (µL) | Concentration |
| --- | --- | --- |
| 20.00 | 2.00 | 1 mg/mL |

Peak identification was based on accurate mass only. Digalloyl catechin, catechin and epicatechin were identified as the major components for cashew testa extract. Procyanidins were detected in the extract as well, including A- and B-type procyanidins, procyanidin tetramer, and procyanidim trimer, with B-type procyanidins being the major component of the procyanidins. Compounds identified, in addition to those just mentioned, included digalloyl catechin, vaccihein A, 6"-p-coumaroylprunin, and dunalianoside B, among others. LC/MS and LC/PDA chromatograms of cashew testa extract obtained from the analysis are illustrated in FIG. 4.

Examples—Bioassay

Extracts of cashew testa were prepared with food-grade ethanol, and then filtered and dried as described above. Research grade reagents were used for the rest of the assay preparations. Extracts were dissolved in dimethyl sulfoxide ('DMSO') to a final concentration of 50 mg/mL, and then diluted in appropriate buffer for each bioassay to working concentrations.

Example 4—COX-1 and COX-2 Inhibition

Cashew testa extract was tested for COX-1 inhibition using the cyclooxygenase-1 ('COX-1') Inhibitor Screening Kit (catalog #K548) from BioVision (Milpitas, Calif., U.S.). This screening kit measures the production of the organic peroxide prostaglandin G2, a product generated by the COX enzyme, over a time course. Extracts were dissolved to working concentrations in DMSO with COX Assay Buffer to a final concentration of 5% DMSO. SC-560 COX-1 inhibitor was used as a positive control. COX-1 enzyme was reconstituted in sterile water and stored at −80° C. COX cofactor and arachidonic acid solutions were diluted just prior to use. COX probe, COX cofactor, and COX-1 enzyme solution were added to the test samples and controls before the arachidonic acid solution was quickly added to start the reaction. Fluorescence was measured every minute for 10 minutes at the following wavelengths: excitation −535 nm, emission 590 nm. The slope of the linear portion of the curve (FIG. 5) was deduced and percent inhibition of the uninhibited control was calculated. Referring to FIG. 5, various degrees of COX-1 inhibition were observed, depending on the concentration of cashew testa extract. Cashew testa extract COX-1 inhibition was observed to be from about 4 µg/mL to at least about 2000 µg/mL, more particularly from about 15 µg/mL to about 250 µg/mL, with an $IC_{50}$ of 32 µg/mL.

Cashew testa extract was tested for COX-2 inhibition using the cyclooxygenase-2 ('COX-2') Inhibitor Screening Kit (catalog #K547) from BioVision (Milpitas, Calif., U.S.). This screening kit measures the production of the organic peroxide prostaglandin G2, a product generated by the COX enzyme, over a time course. Extracts were dissolved to working concentrations in DMSO with COX Assay Buffer to a final concentration of 10% DMSO. Celecoxib nonsteroidal anti-inflammatory drug ('NSAID') was used as a positive control. COX-2 enzyme was reconstituted in sterile water and stored at −80° C. COX cofactor and arachidonic acid solutions were diluted just prior to use. COX probe, COX cofactor, and COX-1 enzyme solution were added to the test samples and controls before the arachidonic acid solution was quickly added to start the reaction. Fluorescence was measured every minute for 10 minutes at the following wavelengths: excitation −535 nm, emission 590 nm. The slope of the linear portion of the curve (FIG. 6) was deduced and percent inhibition of the uninhibited control was calculated. Referring to FIG. 6, various degrees of COX-2 inhibition were observed, depending on the concentration of cashew testa extract. Cashew testa extract COX-2 inhibition was observed to be from about 4 µg/mL to at least about 2000 µg/mL, more particularly from about 30 µg/mL to about 250 µg/mL, with an $IC_{50}$ of 86 µg/mL. Accordingly, based on the results presented herein, cashew testa extract may have reasonable activities in ameliorating the activity or release of COX-1 and COX-2, suggesting its usage in inflammatory diseases mediated by COX-1 and COX-2.

Example 5—5-LOX Inhibition

Cashew testa extract was tested for 5-LOX inhibition using the Lipoxygenase Inhibitor Screening Assay Kit (available from Cayman Chemical, Ann Arbor, Mich., U.S.)

and potato 5-Lipoxygenase enzyme (available from Cayman Chemical). This kit measures hydroperoxides produced in the lipoxygenation reaction.

The extracts were dissolved in methanol to final working concentrations. 5-LOX enzyme, Chromagen, and Linoleic Acid solutions were prepared immediately before use. Nor-dihydroguaiaretic acid ('NDGA') was used as a positive control. 5-LOX enzyme was added to the test samples and controls and incubated for five minutes at room temperature to allow for enzyme/inhibitor interaction. Linoleic acid substrate was added to the plate to initiate the reaction, and the plate was then shaken at room temperature for 10 minutes. Chromagen was added to visualize the hydroperoxides formed during the reaction and the plate was shaken at room temperature for another five minutes. The absorbance was then read at 492 nm. Percent inhibition of the extract concentration was calculated in comparison to the uninhibited control wells.

Cashew testa extract was tested for its 5-LOX inhibition activity at 10 different concentrations (0.7, 1.5, 3.0, 6.0, 11.9, 15.6, 31.2, 62.5, 125.0 and 250.0 µg/mL). NDGA was used as a positive control at 100 µM with a 100% 5-LOX enzyme inhibition. Referring to FIG. 7, cashew testa extract 5-LOX inhibition was observed to be from about 32 µg/mL to at least about 250 µg/mL, more particularly from about 32 µg/mL to about 125 µg/mL, with an $IC_{50}$ of 55 µg/mL observed for the cashew testa extract. Accordingly, based on the results presented herein, cashew testa extract may have reasonable activities in ameliorating the activity or release of 5-LOX, suggesting its usage in inflammatory diseases mediated by 5-LOX.

Example 6—HMGB1 Inhibition

HMGB1 Experimental Procedure—

Cell Culture. Murine macrophage-like cells (available as RAW 264.7 (ATCC® TIB-71™) from American Type Culture Collection (ATCC), Manassas, Va., U.S.) were cultured in Dulbecco's Modified Eagle's Medium ('DMEM') ((DMEM) (ATCC® 30-2002™), from American Type Culture Collection (ATCC), Manassas, Va., U.S.) supplemented with 10% fetal bovine serum (from Atlanta Biologicals, Lawrenceville, Ga., U.S.). The cells were maintained under normoxic conditions (5% $CO_2$/21% $O_2$), allowed to grow to 70-80% confluency, and subcultured every two (2) days.

Extract/Drug Preparation. Cashew testa extract was stored in powder form at −20° C. Prior to treating cells with extract, a stock solution volume of the extract was adjusted to a final concentration of 50 mg/mL in dimethyl sulfoxide ('DMSO') (from AMRESCO, Inc., Solon, Ohio, U.S.) and stored at −20° C. Extract was diluted to a final concentration of 0.25 mg/mL in serum-free Opti-MEM™ I medium (from Gibco-BRL, Gaithersburg, Md., U.S.) and filtered sterilized by 0.2 µm PES syringe filter (from VWR, Radnor, Pa., U.S.). Sodium salicylate (from AMRESCO, Inc., Solon, Ohio, U.S.) was prepared at 2-20 µM as a positive control, which can attenuate hyperoxia-induced HMGB1 release from macrophages.

Hyperoxia Exposure. The exposure of murine macrophage RAW 264.7 cells to hyperoxia was achieved in sealed, humidified Plexiglas chambers (from Billups-Rothenberg, Del Mar, Calif., U.S.) flushed with 95% $O_2$/5% $CO_2$ at 37° C. for 24 hours.

HMGB1 ELISA. To determine the levels of extracellular HMGB1, RAW 264.7 cells were cultured in serum-free Opti-MEM™ I medium (from Gibco-BRL, Gaithersburg, Md., U.S.) in 6-well plates and were kept at either 21% $O_2$ (room air) or exposed to 95% $O_2$ with or without the cashew testa extract for 24 hours. After hyperoxic exposure, the levels of HMGB1 in the culture media were measured by ELISA (enzyme-linked immunosorbent assay). Cell culture media was collected and pelleted at 500 g for 5 minutes at 4° C. Equal volumes of cell culture supernatant were then approximately 6-x's concentrated using Amicon Ultra-4 centrifugal units (from EMD Millipore, Burlington, Mass., U.S.). Just after concentration, equal volumes of cell culture supernatant concentrate were loaded onto a 96-well plate for determination of HMGB1 by ELISA according to manufacturer's instructions (from Chondrex, Inc., Redmond, Wash., U.S.). Plate absorbances were determined by reading the optical density ('OD') value at 450 nm (with 630 nm used as a reference) on a Thermo Multiscan Ex microplate reader (from Thermo Scientific, Waltham, Mass., U.S.). HMGB1 levels were determined in sample cell culture supernatant by comparison to a standard curve and further corrected by applying concentration factors.

Statistical Analysis. Data was presented as the mean ±standard error of the mean (SEM) of one to three independent experiments. Data was analyzed by use of one-way analysis of variance (ANOVA) using Fisher's Least Significant Difference ('LSD') post-hoc analysis and GraphPad Prism version 6 software (from GraftPad Software, La Jolla, Calif., U.S.). A P-Value of <0.05 was considered statistically significant.

HMGB1 Experimental Results—

Referring to FIG. 8, it is seen that hyperoxia ('O2') resulted in a significant increase in HMGB1 level compared to cells treated with 21% $O_2$ ('RA'). These elevated levels of HMGB1 were reduced closer to normal levels (cells exposed to room air (RA) with no treatment) as a result of treatment with cashew testa extract ('CT'). Similar reductions were observed for the positive control sodium salicylate ('SS'). Reductions for both treatment groups (SS and CT) were statistically significant. Accordingly, based on the results presented herein, cashew testa extract may have reasonable activities in ameliorating the activity or release of HMGB1, suggesting its usage in inflammatory diseases mediated by HMGB1.

The above data illustrates that the botanical extract of the testa of *Anacardium occidentale* L. has one or more compounds that exhibit anti-inflammatory activity. More particularly, the cashew testa extract may have reasonable activities in ameliorating the activity or release of COX-1, COX-2, 5-LOX, and/or HMGB1.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Further, unless defined otherwise, all technical and scientific terms used herein have the same meaning as commonly understood to one of ordinary skill in the art to which this invention belongs. Consequently, it is not intended that this invention be limited to the specific embodiments disclosed herein, but that it cover all modifications and alternatives coming within the true scope and spirit of the invention as embodied in the attached claims.

We claim:

1. A method of inhibiting inflammation in a subject comprising:
   administering to the subject a composition comprising the botanical extract of the testa of *Anacardium occidentale L.*,
   wherein the botanical extract has been standardized to a catechin content of about 10.0 w/w % or greater, based on total weight of the extract, and
   wherein the botanical extract is present in the composition in an amount of from about 25.0 μg/mL to about 250.0 μg/mL.

2. The method of claim 1, wherein the composition inhibits COX-1 activity.

3. The method of claim 1, wherein the composition inhibits COX-2 activity.

4. The method of claim 1, wherein the composition inhibits 5-LOX activity.

5. The method of claim 1, wherein the composition inhibits HMGB1 activity.

6. The method of claim 1, wherein the composition is a dietary supplement.

7. The method of claim 6, wherein the dietary supplement is in solid dosage form.

8. The method of claim 1, wherein the composition is a topical composition.

* * * * *